(12) United States Patent
Miyagi et al.

(10) Patent No.: US 7,981,027 B2
(45) Date of Patent: Jul. 19, 2011

(54) ENDOSCOPE AND FRONT COVER

(75) Inventors: Masaaki Miyagi, Tokyo (JP); Hiroki Moriyama, Tokyo (JP); Seisuke Takase, Tokyo (JP)

(73) Assignee: Olympus Corporation (JP)

( * ) Notice: Subject to any disclaimer, the term of this patent is extended or adjusted under 35 U.S.C. 154(b) by 1105 days.

(21) Appl. No.: 11/627,526

(22) Filed: Jan. 26, 2007

(65) Prior Publication Data

US 2007/0135682 A1     Jun. 14, 2007

Related U.S. Application Data

(63) Continuation of application No. PCT/JP2005/013662, filed on Jul. 26, 2005.

(30) Foreign Application Priority Data

Jul. 27, 2004  (JP) .................................. 2004-219215

(51) Int. Cl.
*A61B 1/00*     (2006.01)
(52) U.S. Cl. ........ 600/129; 600/156; 600/164; 600/176; 600/177
(58) Field of Classification Search .................. 600/129, 600/176, 171, 177, 160, 182, 156, 153, 146
See application file for complete search history.

(56) References Cited

U.S. PATENT DOCUMENTS

| | | | | |
|---|---|---|---|---|
| 4,733,937 A | * | 3/1988 | Lia et al. ........................ | 385/117 |
| 5,871,440 A | * | 2/1999 | Okada ........................... | 600/129 |
| 5,879,288 A | * | 3/1999 | Suzuki et al. ................ | 600/176 |
| 5,891,014 A | * | 4/1999 | Akiba ............................ | 600/158 |
| 6,095,971 A | * | 8/2000 | Takahashi ..................... | 600/159 |
| 6,184,923 B1 | * | 2/2001 | Miyazaki ....................... | 348/75 |
| 6,476,851 B1 | | 11/2002 | Nakamura | |
| 2004/0153098 A1 | * | 8/2004 | Chin et al. .................... | 606/129 |
| 2006/0229497 A1 | * | 10/2006 | Toyama ........................ | 600/156 |

FOREIGN PATENT DOCUMENTS

| | | |
|---|---|---|
| EP | 1 774 895 | 4/2007 |
| JP | 04-102432 | 4/1992 |
| JP | 2001-258823 | 9/2001 |
| JP | 2002-085326 | 3/2002 |
| JP | 2005-192638 | 7/2005 |
| KR | 1998-702699 | 8/1998 |
| WO | PCT/US95/02663 | 3/1995 |

OTHER PUBLICATIONS

International Search Report PCT/JP2005/013662 dated Sep. 15, 2005 (Japanese Patent Office).
Extended European Search Report dated Sep. 22, 2009 in corresponding European Patent Application No. EP 05 76 7377.

* cited by examiner

*Primary Examiner* — Matthew J Kasztejna
(74) *Attorney, Agent, or Firm* — Ostrolenk Faber LLP

(57) ABSTRACT

An endoscope includes an observation window for observing an image of a photographic subject; an illumination window for emitting illumination light for illuminating the photographic subject; a suction port connected to a suction channel are provided on a distal end surface of an insertion portion; an observation window peripheral edge portion which is formed so that a surface having the observation window is vertical to an observation light axis; an illumination window peripheral edge portion which is formed so that a surface having the illumination window is vertical to an illumination light axis which tilts outward with respect to the observation light axis; and a suction port peripheral edge portion which is formed so that a surface having the suction port is flush with the observation window peripheral edge portion.

6 Claims, 7 Drawing Sheets

ENDOSCOPE AND FRONT COVER

CROSS-REFERENCE TO RELATED APPLICATIONS

This application is a continuation of PCT international application Ser. No. PCT/JP2005/013662 filed Jul. 26, 2005 which designates the United States, incorporated herein by reference, and which claims the benefit of priority from Japanese Patent Application No. 2004-219215, filed Jul. 27, 2004, incorporated herein by reference.

BACKGROUND OF THE INVENTION

1. Field of the Invention

The present invention relates to an endoscope having a wide viewing angle and a suction channel for suctioning waste materials or the like in a body cavity such as large intestine, and a front cover.

2. Description of the Related Art

Conventionally, endoscopes are used widely in the medical field or the like. For example, a long and narrow insertion portion of an endoscope is inserted into a body cavity, so that organs or the like in the body cavity can be observed, and various treatments can be given by using treatment instruments which are inserted into a treatment instrument insertion channel as the need arises. A distal end of the insertion portion is provided with a bendable portion, and an operation portion of the endoscope is operated so that an observing direction of an observation window at the distal end can be changed.

A viewing angle of conventional endoscopes is about 120 to 140°, and an operator observes a body cavity by means of an observing image at its viewing angle. However, when the operator desires to observe a portion which is out of the visual field range while observing the body cavity, the operator curves the bendable portion so as to observe the portion which is out of visual field range.

On the other hand, an endoscope whose viewing angle is further widened in order to observe a wider range is also proposed (for example, Japanese Patent Application Laid-Open No. 2001-258823).

Japanese Patent Application Laid-Open No. 2001-258823 discloses an endoscope where an observation optical system having a wide viewing angle of about 140° to 210° is disposed at a distal end portion. In the document, according to the widening of the angle of the observation optical system, an illumination optical system which is disposed at the distal end portion and illuminates a body cavity is disposed so that its optical axis is overlapped with the optical axis of the observation optical system which tilts at a predetermined angle in order to illuminate an entire observation portion in the body cavity. That is, the distal end portion of the endoscope insertion portion is formed into a so-called cannon shape where a distal end surface through which the optical axis of the observation optical system passes is the most distal end, and the surface of the illumination optical system is disposed on the tapered surface. Further, the distal end surface of the endoscope insertion portion serves also as the treatment instrument insertion channel, and has an opening of a suction channel for suctioning waste materials, mucous membrane and the like in the body cavity such as large intestine.

SUMMARY OF THE INVENTION

An endoscope according to one aspect of the present invention includes an observation window for observing an image of a photographic subject; an illumination window for emitting illumination light for illuminating the photographic subject; a suction port connected to a suction channel are provided on a distal end surface of an insertion portion; an observation window peripheral edge portion which is formed so that a surface having the observation window is vertical to an observation light axis; an illumination window peripheral edge portion which is formed so that a surface having the illumination window is vertical to an illumination light axis which tilts outward with respect to the observation light axis; and a suction port peripheral edge portion which is formed so that a surface having the suction port is flush with the observation window peripheral edge portion.

An endoscope according to another aspect of the present invention includes an observation window for observing an image of a photographic subject; an illumination window for emitting illumination light for illuminating the photographic subject; a suction port connected to a suction channel are provided on a distal end surface of an insertion portion; an observation window peripheral edge portion which is formed so that a surface having the observation window is vertical to an observation light axis; an illumination window peripheral edge portion which is formed so that a surface having the illumination window is vertical to an illumination light axis which tilts with respect to the observation light axis; and a suction port peripheral edge portion which is formed so that a surface having the suction port and the observation window peripheral edge portion form an angle more acute than a tilt angle of the illumination window peripheral edge portion with respect to the observation window peripheral edge portion.

A front cover according to still another aspect of the present invention includes an observation window for observing an image of a photographic subject; an illumination window for emitting illumination light for illuminating the photographic subject; a suction port connected to a suction channel so as to cover a distal end portion of an insertion portion of an endoscope; an observation window peripheral edge portion which is formed so that a surface having the observation window is vertical to an observation light axis; an illumination window peripheral edge portion which is formed so that a surface having the illumination window is vertical to an illumination light axis which tilts outward with respect to the observation light axis; and a suction port peripheral edge portion which is formed so that a surface having the suction port is flush with the observation window peripheral edge portion.

A front cover according to still another aspect of the present invention includes an observation window for observing an image of a photographic subject; an illumination window for emitting illumination light for illuminating the photographic subject; a suction port connected to a suction channel so as to cover a distal end portion of an insertion portion of an endoscope; an observation window peripheral edge portion which is formed so that a surface having the observation window is vertical to an observation light axis; an illumination window peripheral edge portion which is formed so that a surface having the illumination window is vertical to an illumination light axis which tilts with respect to the observation light axis; and a suction port peripheral edge portion which is formed so that a surface having the suction port and the observation window peripheral edge portion forms an angle of more acute than a tilt angle of the illumination window peripheral edge portion with respect to the observation window peripheral edge portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An exemplary embodiment of the present invention will be explained below with reference to the drawings.

Figure 1:
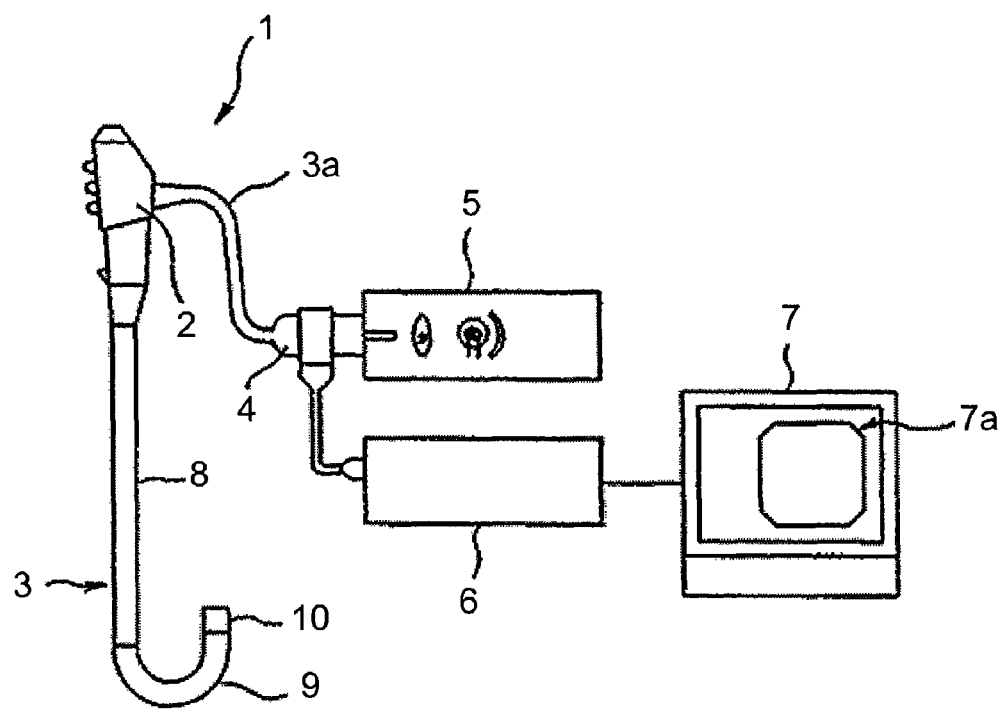
FIG. 1 is an explanatory diagram schematically illustrating an endoscope apparatus.

A constitution of an endoscope apparatus according to the embodiment will be explained below with reference to FIG. 1. FIG. 1 is an explanatory diagram schematically illustrating an endoscope apparatus according to the embodiment of the present invention. As shown in FIG. 1, the endoscope apparatus according to the embodiment has an electronic endoscope (hereinafter, simply "endoscope") 1, a light source device 5, a processor 6 and a monitor 7. The endoscope 1 has an operation portion 2 which controls a curving operation and various pipe lines, an insertion portion 3 whose proximal end is connected to the operation portion 2 and which is inserted into a body cavity, and a universal cord 3a which extends from the operation portion 2 and has a connector portion 4 at its distal end. The connector portion 4 is connected with the light source device 5 and the processor 6. The monitor 7 is connected to the processor 6.

The insertion portion 3 of the endoscope 1 has a flexible pipe section 8 having flexibility, a bendable portion 9 which is provided to a distal end side of the flexible pipe section 8, and a distal end portion 10 which is provided to a distal end side of the bendable portion 9. A distal end surface 11 of the distal end portion 10 is formed into an approximately cannon shape, and contains an imaging unit 40 (see FIG. 3).

The imaging unit 40 has an imaging device such as CCD or CMOS which picks up an image of a portion in a body cavity, and an image signal picked up by the imaging device is transmitted to the processor 6 via the universal cord 3a. The processor 6 processes the transmitted image signal, and allows an observed image 7a to be displayed on the monitor 7.

Further, operation knobs for remotely bending the bendable portion 9, and push button switches or the like for performing various operations represented by air supply and water supply are arranged on the operation portion 2.

The light source device 5 has an illumination light source, and is connected to the operation portion 2, the insertion portion 3 and a light guide (not shown) disposed in the universal cord 3a via the connector portion 4. Further, in this embodiment, the light source device 5 contains an air/water supply source and a suction source for supplying air and water and suctioning them to/from the pipe lines disposed in the endoscope 1.

Figure 2:
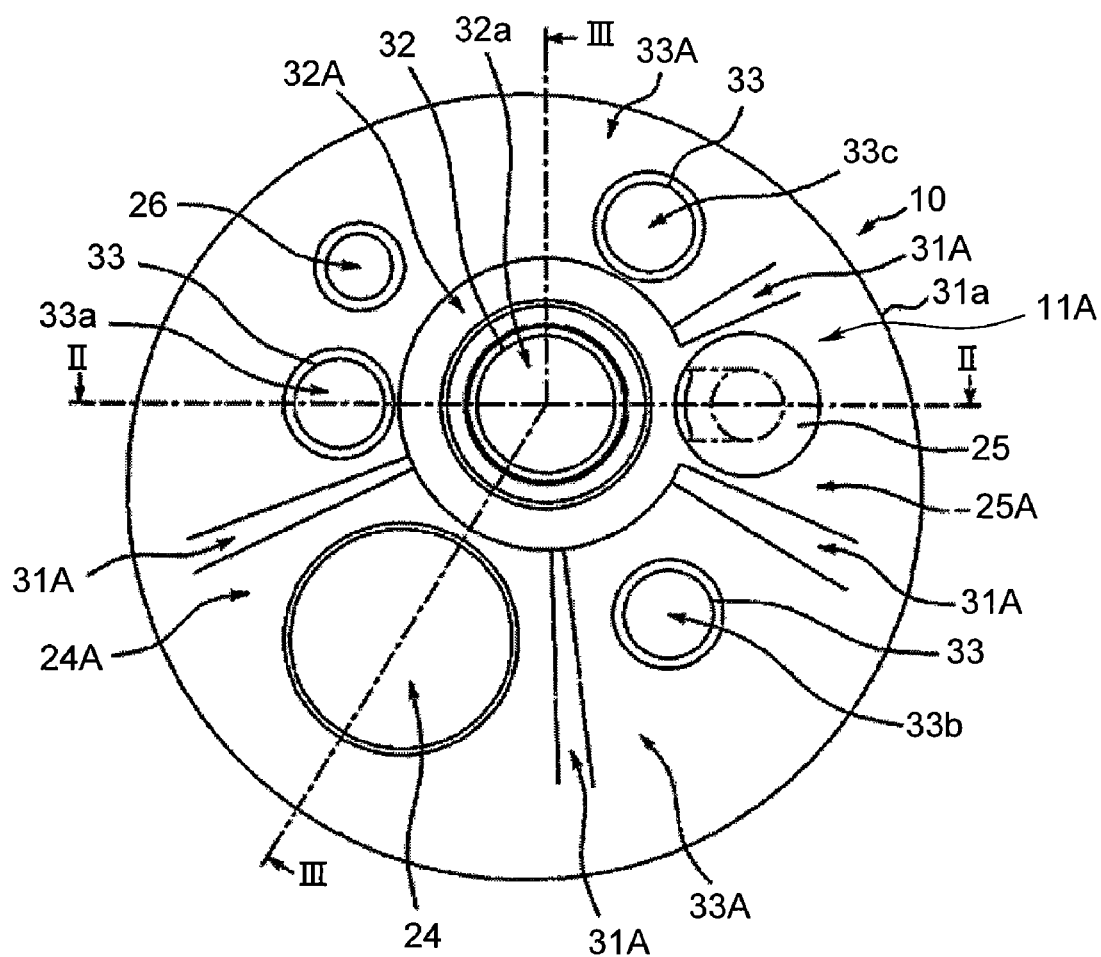
FIG. 2 is a front view of a distal end surface of a distal end portion.
Figure 3:
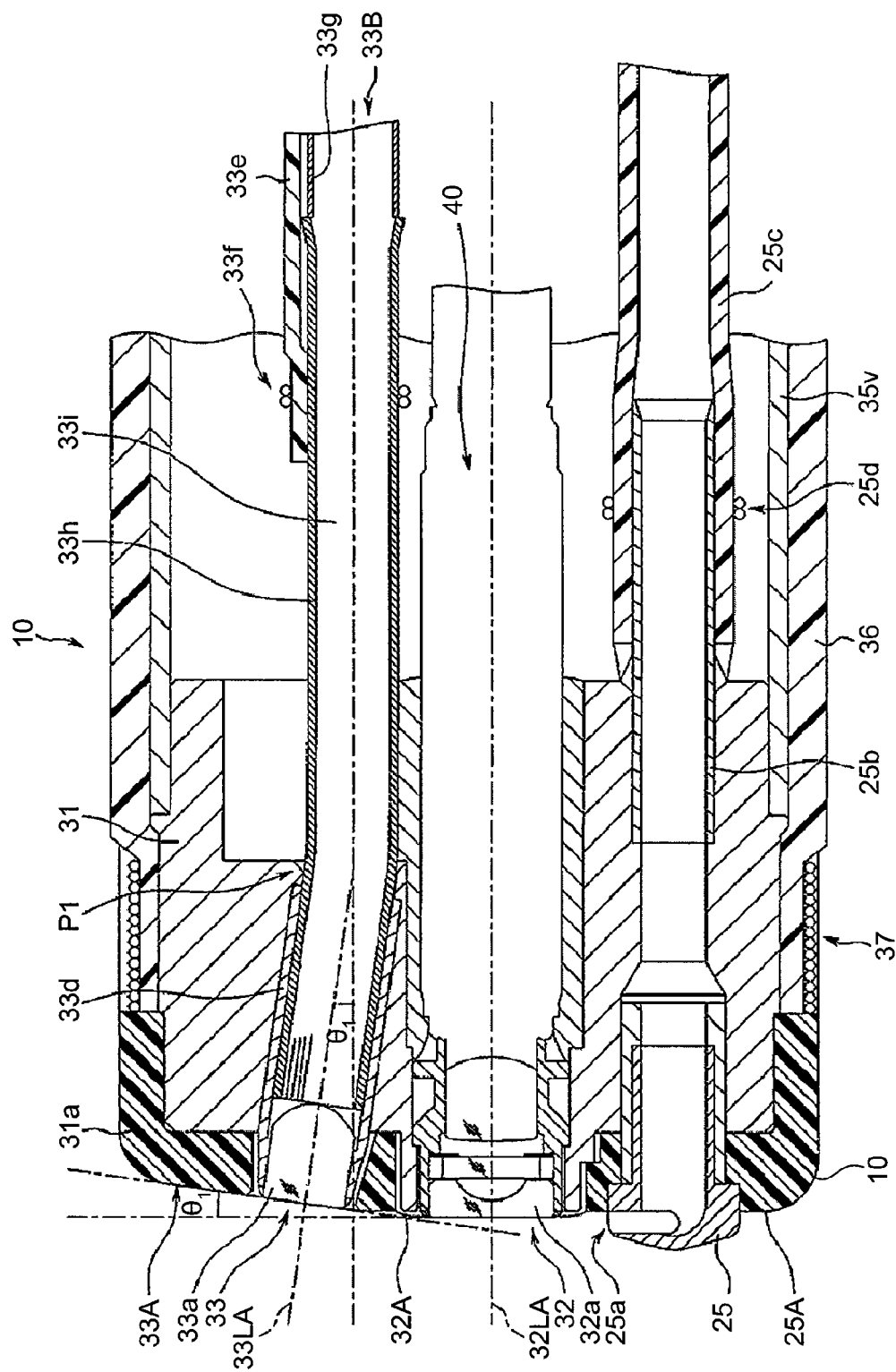
FIG. 3 is a partially sectional view of the distal end portion taken along line II-II in FIG. 2.
Figure 4:
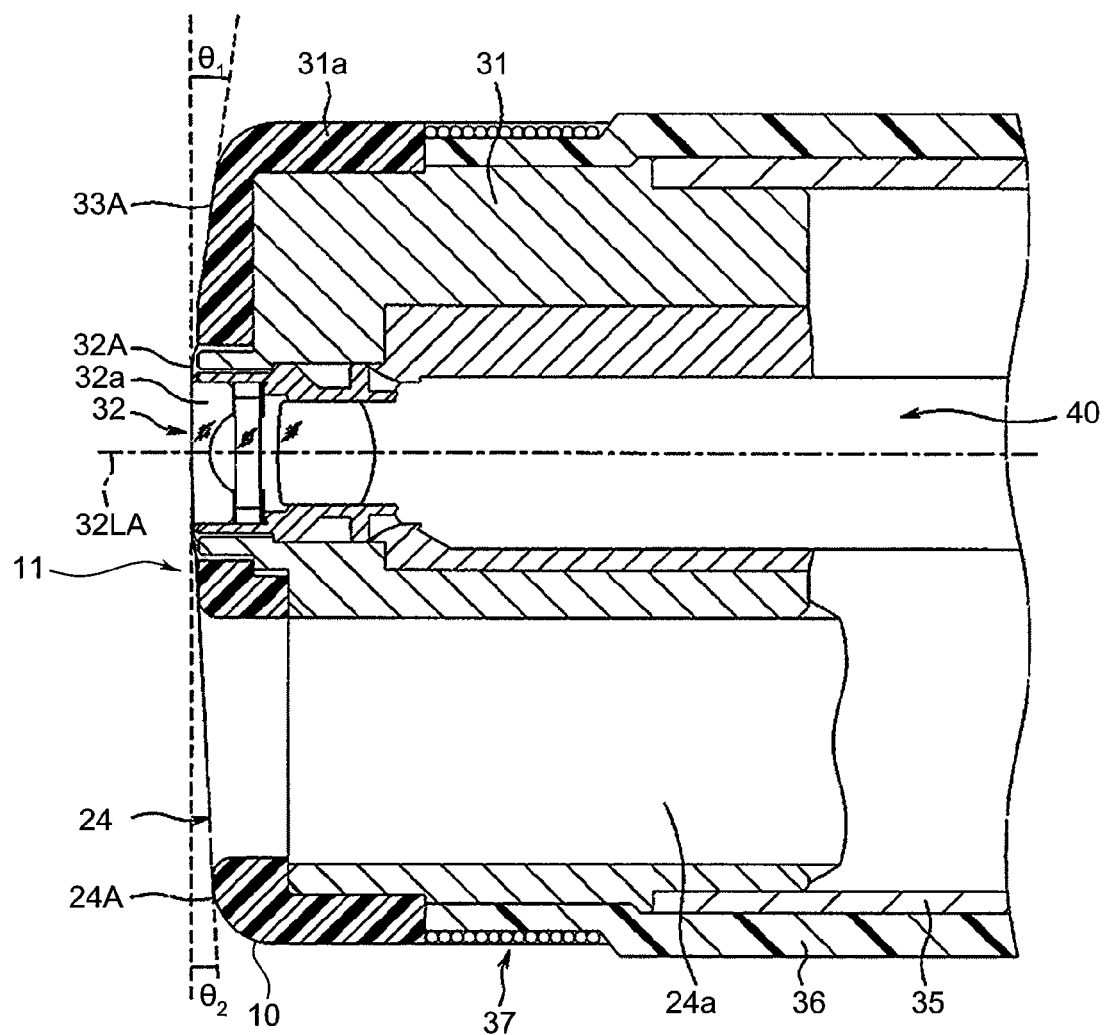
FIG. 4 is a partially sectional view of the distal end portion taken along line III-III in FIG. 2.

The distal end surface of the distal end portion 10 and an internal constitution of the distal end portion 10 will be explained below with reference to FIGS. 2 to 4. FIG. 2 is a front view of the distal end surface of the distal end portion, FIG. 3 is a partially sectional view of the distal end portion taken along line II-II in FIG. 2, and FIG. 4 is a partially sectional view of the distal end portion taken along line III-III in FIG. 2.

As shown in FIG. 2, disposed on the distal end surface (the distal end surface of a front cover 31a, mentioned later) 11 of the distal end portion 10 are an observation lens 32a disposed on an observation window 32, illumination window lenses 33a, 33b and 33c as illumination means which are disposed on, for example, three illumination windows 33, a suction port 24 which also serves as an opening for treatment instruments or the like, an air/water supply nozzle (hereinafter, simply water supply nozzle) 25 for supplying air or water so as to rinse out pollution of an objective lens 32a when the insertion portion 3 is inserted into the body cavity, and a forward water supply port 26 for rinsing out blood and mucosal fluid of a diseased part in the body cavity. Therefore, a plurality of openings for disposing the objective lens 32a, the three illumination window lenses 33a, 33b and 33c, the suction port 24, the water supply nozzle 25 and the forward water supply port 26 are provided on the distal end surface 11 of the distal end portion 10.

The illumination window lenses 33a, 33b and 33c are arranged near an peripheral edge of the objective lens 32a at an interval of a predetermined angle. Further, the suction port 24, the water supply nozzle 25 and the forward water supply port 26 are disposed respectively between the illumination windows 33.

Concretely, the suction port 24 is disposed between the illumination window lens 33a and the illumination window lens 33b, the water supply nozzle 25 is disposed between the illumination window lens 33b and the illumination window lens 33c, and the forward water supply port 26 is disposed between the illumination window lens 33a and the illumination window lens 33c.

A constitution of the distal end portion 10 will be explained below with reference to FIGS. 3 and 4.

As shown in FIG. 3, a distal end rigid portion 31, which has a space capable of disposing the imaging unit 40 corresponding to the observation window 32 and a light guide or the like corresponding to the three illumination windows 33 into the distal end portion 10, is provided into the distal end portion 10. The distal end rigid portion 31 is covered with the front cover 31a, and the front cover 31a covers the distal end side of the distal end rigid portion 31. The imaging unit 40 is inserted and fixed into the distal end rigid portion 31. The imaging unit 40 has an observation optical system composed of an observation window lens and a plurality of lenses, a cover glass and an imaging device such as CCD or CMOS. An observation viewing angle by means of the imaging unit 40 is set to a wide angle of about 140 to 170°.

The imaging device transmits the image signal to the processor 6 by means of light which enters via the observation window 32, but the processor 6 image-processes the received image signal so as to create data of an observation image 7a having a substantially rectangular shape. As shown in FIG. 1, four corners of the rectangular observation image 7a are scraped off, so that the observation image 7a is electronically masked and is displayed as an octagonal observation image on the monitor 7. An optical system of the imaging unit 32 is designed in the observation visual field of the imaging unit 40 so that the water supply nozzle 25 does not enter.

A light guide unit 33B is composed of the illumination window lens 33a and an optical fiber bundle 33i as the light guide. The distal end portion of the optical fiber bundle 33i is fixed into a metallic pipe 33h by adhesive or the like. The distal end portion of the optical fiber bundle 33i and the illumination window lens 33a are inserted into a frame 33d and are fixed.

The light guide unit 33B is fixed to the distal end rigid portion 31 by a fixing screw (not shown). The optical fiber bundle 33i from a proximal end side of the metallic pipe 33h is covered with a flexible tube 33g, and further a part of the metallic pipe 33h and the tube 33g are covered with an outer tube 33e.

The outer tube 33e is fixed to the metallic pipe 33h by a string 33f. The metallic pipe 33h is bent at a halfway position P1 to an outer periphery side of the distal end portion 10 at a predetermined angle θ1. The angle θ1 is, for example, about 8°. As a result, the optical fiber bundle 33i is bent along the bent shape of the metallic pipe 33h.

Therefore, a light axis 33LA at the approximately center of an emission range by means of the illumination means such as the illumination window lens 33a for emitting illumination light (hereinafter, for convenience of the explanation, this axis is an illumination light axis 33LA) is not completely parallel with a light axis 32LA of the observation optical system such as the observation window lens of the imaging unit (hereinafter, for convenience of the explanation, this axis is an observation light axis 32LA).

That is, as to the illumination light axis 33LA, the light axis which is parallel with the observation light axis 32LA is set on the proximal end side with respect to the position P1, and tilts towards the distal end from the position P1 by the angle θ1 with respect to the observation light axis 32LA. More specifically, a distal end direction of the illumination light axis 33LA tilts in a direction separated from an edge point of an observation direction of the observation light axis 32LA of the imaging unit at the predetermined angle θ1 with respect to the observation light axis 32LA.

As to the illumination light axes of the light guide unit 33B corresponding to the other illumination window lenses 33b and 33c, their distal end directions tilt in a direction separated from the edge point in the observation direction of the observation light axis 32LA of the imaging unit at the angle θ1 with respect to the observation light axis 32LA. Therefore, the illumination range of the light guide unit 33B is set correspondingly to the wide visual field range of the imaging unit. Instead of the light guide unit 33B as the illumination means, an illumination member such as LED may be adopted.

Further, as to the front cover 31a, the distal end surface 11 is formed so that the window surface of the observation window 32 is vertical to the observation light axis 32LA and the window surface of the illumination window 33 is vertical to the illumination light axis 33LA. That is, the observation window lens 32a is disposed on the observation window 32 so that its surface is substantially flush with the window surface of the observation window 32 of the front cover 31a.

On the other hand, the illumination window lens 33a is disposed on the illumination window 33 so that its lens surface is substantially flush with the window surface of the illumination window 33 of the front cover 31a. Namely, as to the front cover 31a, an opening surface of the illumination window 33 tilts towards the proximal end side at the predetermined angle θ1 (for example, about 8°) with respect to an opening surface of the observation window 32. A vicinity around the observation window 32 of the front cover 31a has an observation window peripheral edge portion 32A whose surface is flush with the opening surface of the observation window 32. A vicinity around the observation window 33 of the front cover 31a has an observation window peripheral edge portion 33A whose surface is flush with the opening surface of the observation window 33.

The distal end portion of the water supply nozzle 25 is provided with an opening 25a. The opening 25a is provided so that water ejected from the water supply nozzle 25 is supplied in a direction substantially parallel with the plane perpendicular to the light axis 32LA and a direction passing through the surface of the observation window lens 32a on the observation window 32. The proximal end side of the water supply nozzle 25 has a pipe shape and is connected to the water supply tube 25c via a connecting pipe 25b. Therefore, the connecting pipe 25b and the water supply tube 25c form a water supply pipe line. The water supply tube 25c is fixed to the connecting pipe 25b by a string 25d.

The proximal end side of the distal end rigid portion 31 is fixed to a part of a bending piece 35. The proximal end side of the distal end rigid portion 31 and the bending piece 35 are covered with an outer tube 36 formed by synthetic resin or rubber. The outer tube 36 is fixed to the distal end rigid portion 31 by a string 37.

As shown in FIG. 4, the suction port 24 disposed on the front cover 31a of the distal end portion 10 is an opening of the suction channel 24a serving also as the treatment instrument channel inserted towards the proximal end side. The suction channel 24a is inserted into the insertion portion 3, the operation portion 2, the universal cord 3a and the connector portion 4 so as to be connected to a suction source of the light source device 5. The suction channel 24a is also connected to a treatment instrument insertion port disposed on the operation portion 2.

The opening surface of the suction port 24 of the front cover 31a tilts towards the proximal end side at a predetermined angle θ2 with respect to the window surface of the observation window 32. The angle θ2 is, for example, about 2° to 3°. Therefore, as to the front cover 31a, the opening surface of the suction port 24 tilts towards the proximal end side at the predetermined angle θ2 with respect to the opening surface of the observation window 32. The front cover 31a has a suction port peripheral edge portion 24A formed in the same plane as the opening surface of the suction port 24 near a periphery of the suction port 24.

A vicinity of the front cover 31a provided with the water supply nozzle 25 on the distal end surface 11 has a water supply nozzle peripheral edge portion 25A whose surface is formed in the same plane as the opening surface of the observation window 32. That is, the surface of the water supply nozzle peripheral edge portion 25A is flush with the surface of the observation window peripheral edge portion 32A. Further, the surface of the water supply nozzle peripheral edge portion 25A may be flush with the surface of the illumination window peripheral edge portion 33A or the surface of the suction port peripheral edge portion 24A, or may be in the plane between the surface of the observation window peripheral edge portion 32A and the illumination window peripheral edge portion 33A.

Figure 5:
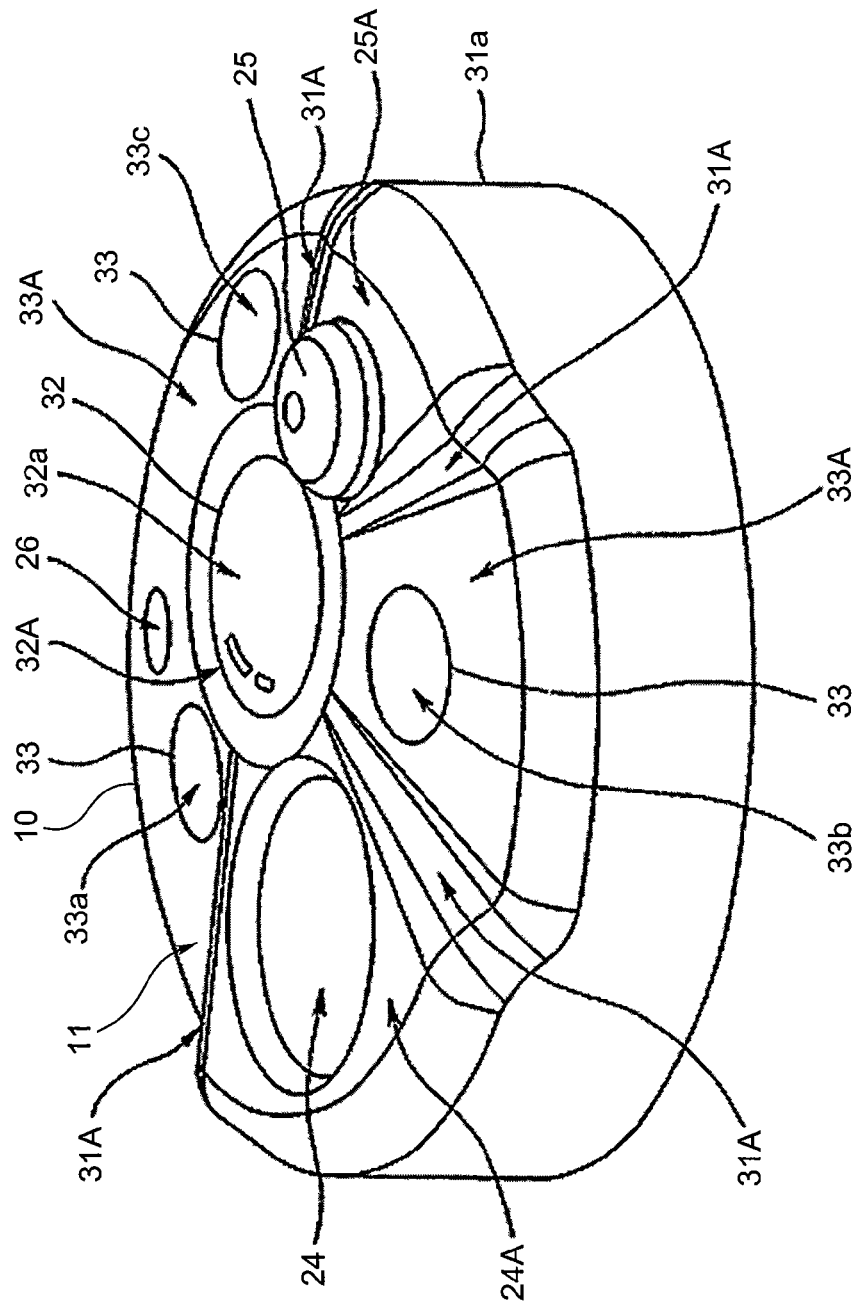
FIG. 5 is a perspective view of a front cover.

Therefore, the front cover 31a having the peripheral edge portions 24A, 25A, 32A, and 33A on the distal end surface 11, as shown in FIG. 5, has a so-called distal end cannon shape such that the respective peripheral edge portions 24A, 25A, 32A, and 33A tilt from the center of the observation window 32 towards the peripheral edge at the predetermined angles. Further, boundary surfaces 31A as smooth curved surfaces or tilt surfaces are formed respectively on boundary portions of the peripheral edge portions 24A, 25A, 32A, and 33A of the front cover 31a in order to reduce steps. Further, the front cover 31a is formed so that corner shape on the boundary between the outer peripheral section of the distal end surface 11 and the outer peripheral surface has a smooth curved shape.

In the case where an endoscopic examination is carried out by the endoscope 1, the insertion portion 3 of the endoscope 1 is inserted into a body cavity such as large intestine. At this time, the distal end portion 10 reaches an portion in the body cavity into which the insertion portion 3 is being inserted and a portion to be examined, and mucous membrane, waste materials and the like of the body cavity adhere to the surface of the observation window lens 32a at the time of various treatments and observations, thereby occasionally interrupting a visual field of an endoscopic image obtained by the imaging unit. For this reason, the mucous membrane, the waste materials and the like of the body cavity should be suctioned via the distal end surface 11 of the insertion portion 3, namely, the suction port 24 of the front cover 31a.

Figure 6:
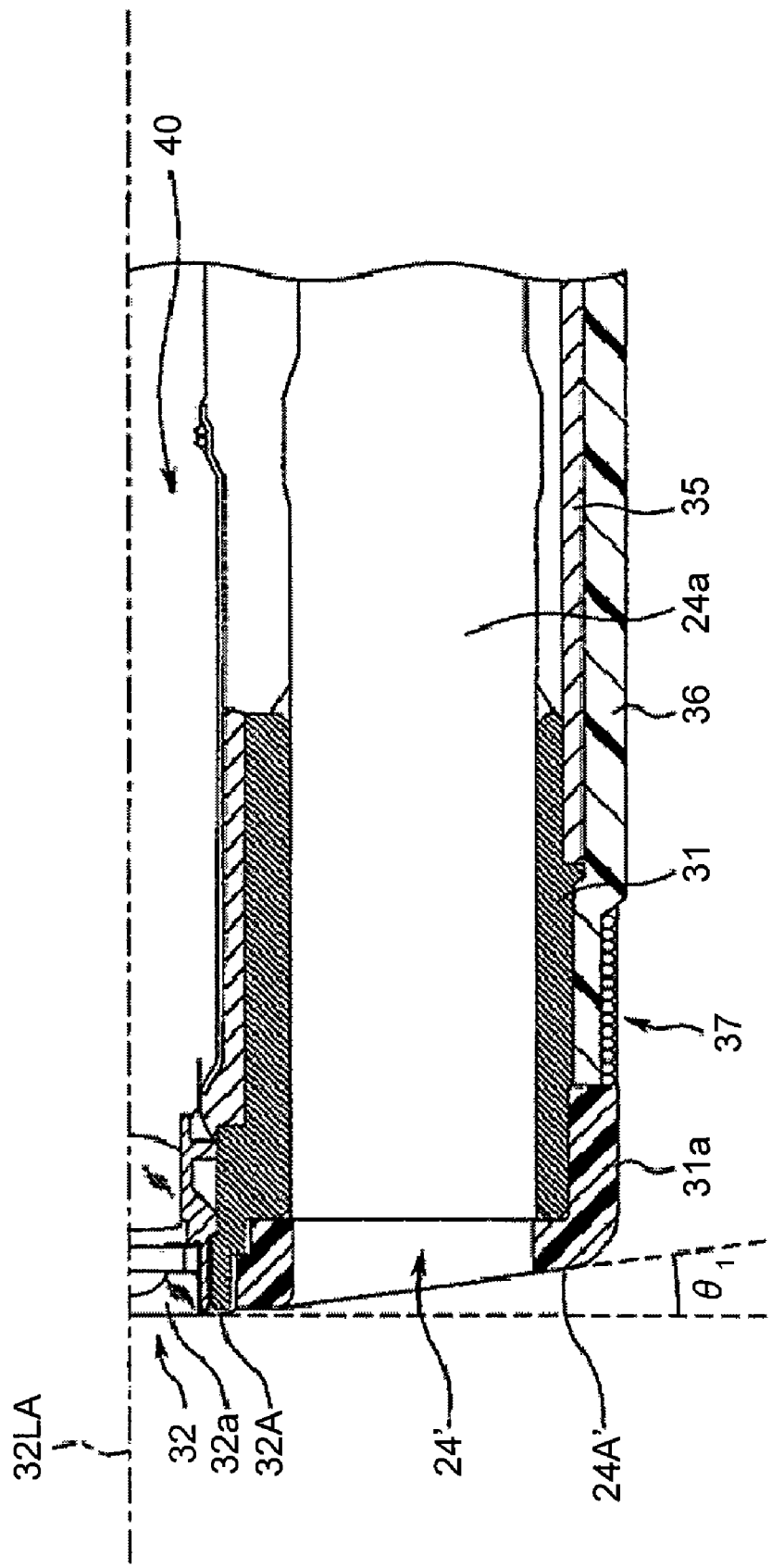
FIG. 6 is a partially sectional view of the distal end portion for explaining a suction port of a conventional endoscope.

In a conventional endoscope having a wide visual field, as shown in FIG. 6, the opening surface of a suction port 24' of a front cover 31a tilts towards a proximal end side at an angle θ1 with respect to a window surface of the observation window 32. That is, the opening surface of the suction port 24' is flush with an illumination window peripheral edge portion (not shown) of the front cover 31a. Therefore, also a suction port peripheral edge portion 24A' of the front cover 31a is flush with the illumination window peripheral edge portion. More specifically, as to the front cover 31a, a surface which tilts at the tilt angle θ1 with respect to the window surface of an observation window 32 is formed around the illumination window (not shown) and the suction port 24'. In the conventional endoscope, when mucous membrane, waste materials and the like of a body cavity are suctioned via the suction port 24', a body cavity wall is suctioned since the tilt angle θ1 of the suction port 24' with respect to the window surface of the observation window 32 is large. As a result, the suction force for the mucous membrane, the waste materials of the body cavity is weakened.

Figure 7:
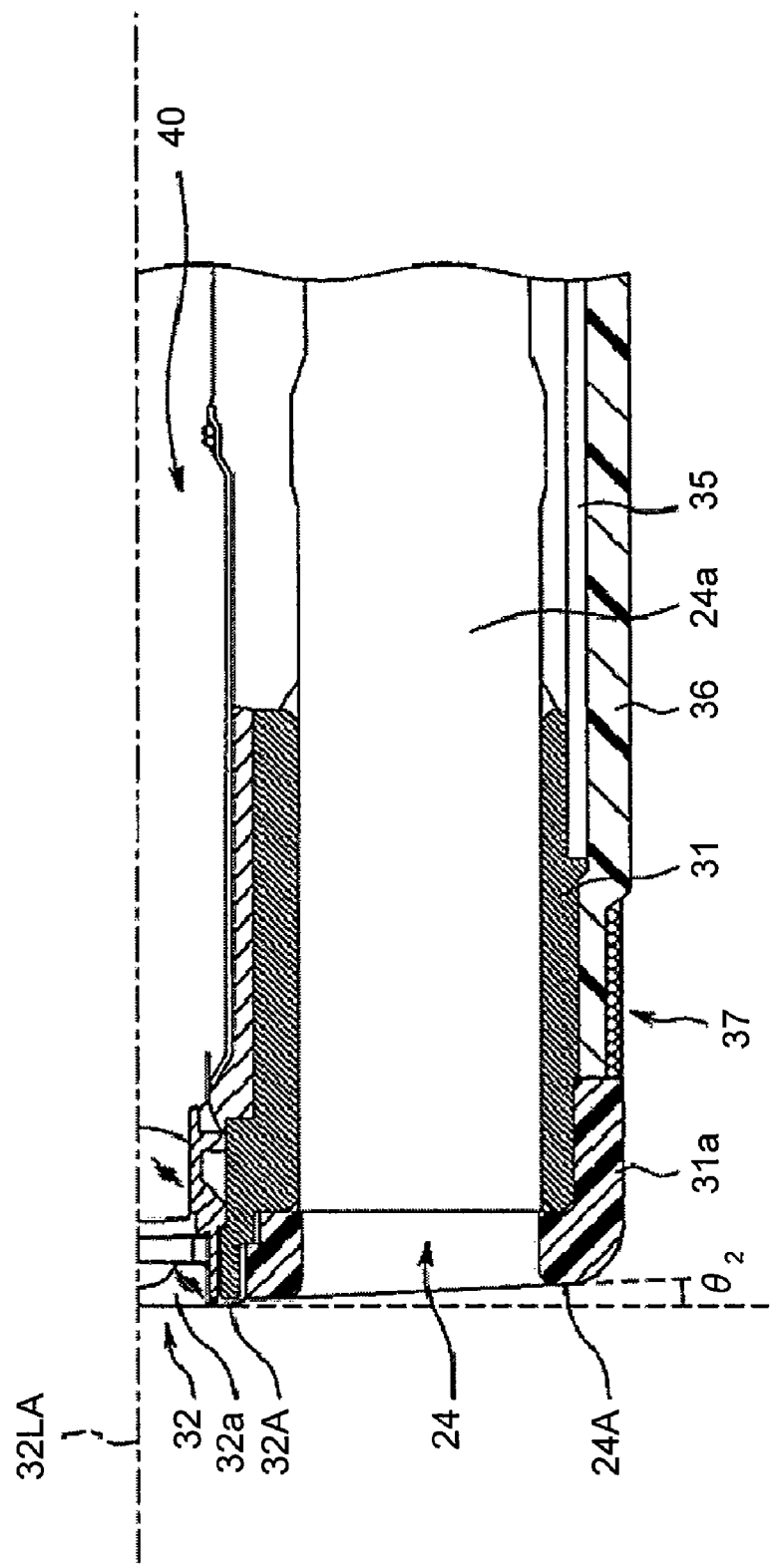
FIG. 7 is a partially sectional view of the distal end portion for explaining a suction port of the endoscope of the present invention.

Therefore, as shown also in FIG. 7, as to the endoscope 1 of this embodiment having the above constitution, the tilt angles of the opening surface of the suction port 24 and the surface of the suction port peripheral edge portion 24A with respect to the window surface of the observation window 32 of the front cover 31a are angle θ2 (for example, about 2 to 3°). That is, the tilt angles of the opening surface of the suction port 24 of the front cover 31a and the surface of the suction port peripheral edge portion 24a with respect to the window surface of the observation window 32 are the acute angle θ2. On the other hand, in order to sufficiently secure the illumination range corresponding to the image pickup range, the tilt angles of the opening surface of the illumination window 33 of the front cover 31a, the surfaces of the illumination window lenses 33a to 33c and the surface of the illumination window peripheral edge portion 33A with respect to the window surface of the observation window 32 are the angle θ larger than the angle θ2 according to the angle θ1 at which the illumination light axis 33LA tilts with respect to the observation light axis 32LA (for example, about 8°).

In other words, the angle θ2 at which the opening surface of the suction port 24 and the surface of the suction port peripheral edge portion 24A tilt with respect to the window surface of the observation window 32 is more acute than the angle θ1 at which the opening surface of the illumination window 33, the surfaces of the illumination window lenses 33a to 33c and the surface of the illumination window peripheral edge portion 33A tilt with respect to the window surface of the observation window 32. As a result, since the opening of the suction port 24 is next to vertical to the body cavity wall, a gap between the suction port 24 and the body cavity wall is widened at the time of suctioning the mucous membrane and the waste materials of the body cavity, so that the sufficient suction force can be exercised without disturbing the absorption force by means of the body cavity wall.

As a consequence, the endoscope 1 of this embodiment can secure the illumination range sufficient for the image pickup range with wide viewing angle, can prevent absorption of the body cavity wall to the opening of the suction channel as much as possible at the time of suctioning waste materials, the mucous membrane and the like of the body cavity and can restrain weakening of the suction force.

Further, the boundary surfaces 31A as the smooth curved surfaces or the tilt surfaces are formed respectively on the boundary portions of the peripheral edge portions 24A, 25A, 32A, and 33A of the front cover 31a. For this reason, even if the surface of the front cover 31a has unevenness due to the peripheral edge portions 24A, 25A, 32A, and 33A, adhesion of the mucous membrane, the waste materials and the like of the body cavity can be reduced.

The angle θ1 at which the illumination light axis 33LA tilts with respect to the observation light axis 32LA is variously set so that the illumination range corresponding the image pickup range can be sufficiently secured according to the viewing angle of the imaging unit. Accordingly, the tilt angles of the opening surface of the illumination window 33 of the front cover 31a, the surfaces of the illumination window lenses 33a to 33c and the surface of the illumination window peripheral edge portion 33A with respect to the window surface of the observation window 32 are set to the angle θ1.

Further, the present invention is not limited only to the above-mentioned embodiment, and can be variously changed without departing from the gist of the present invention.

For example, in the embodiment, the angle θ2 (2 to 3°) at which the opening surface of the suction port 24 and the surface of the suction port peripheral edge portion 24A tilt with respect to the window surface of the observation window 32 is provided, and the angle θ2 becomes more acute than the angle θ1 (8°) at which the opening surface of the illumination window 33, the surfaces of the illumination window lenses 33a to 33c and the surface of the illumination window peripheral edge portion 33A tilt with respect to the window surface of the observation window 32, but the constitution is not limited to this. Concretely, the opening surface of the suction port 24 and the surface of the suction port peripheral edge portion 24A do not tilt with respect to the window surface of the observation window 32 but are flush with it (namely, the angle θ2=0°). The opening surface of the illumination window 33, the surfaces of the illumination window lenses 33a to 33c and the surface of the illumination window peripheral edge portion 33A tilt at the angle θ1 (5 to 6°) with respect to the window surface of the observation window 32. In such a constitution, the above-mentioned effect can be produced similarly.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an observation window for observing an image of a photographic subject;
    an illumination window for emitting illumination light for illuminating the photographic subject;
    a suction port connected to a suction channel, wherein the observation window, the illumination window, and the suction port are provided on a distal end surface of an insertion portion;
    an observation window peripheral edge portion which is formed so that a surface having the observation window is vertical to an observation light axis;
    an illumination window peripheral edge portion which is formed so that a surface having the illumination window is vertical to an illumination light axis which tilts with respect to the observation light axis; and
    a suction port peripheral edge portion which is formed so that a surface having the suction port and the observation window peripheral edge portion form an angle more acute than a tilt angle of the illumination window peripheral edge portion with respect to the observation window peripheral edge portion,
    wherein the illumination window peripheral edge portion is provided at a tilt angle of about 8° with respect to the observation window peripheral edge portion and the suction port peripheral edge portion is provided at a tilt angle of 2 to 3° with respect to the observation window peripheral edge portion.

2. The endoscope according to claim 1, wherein a boundary portion between the illumination window peripheral edge portion and the suction port peripheral edge portion is formed into a curved surface shape or a tilt surface shape.

3. The endoscope according to claim 1, wherein the observation window peripheral edge portion is formed at an approximately center of the distal end surface, the illumination window peripheral edge portion is formed so as to tilt backward around the observation window peripheral edge portion, and the suction port peripheral edge portion is formed so as to tilt backward with respect to the illumination window peripheral edge portion.

4. A front cover comprising:
    an observation window for observing an image of a photographic subject;
    an illumination window for emitting illumination light for illuminating the photographic subject;
    a suction port connected to a suction channel so as to cover a distal end portion of an insertion portion of an endoscope,
    an observation window peripheral edge portion which is formed so that a surface having the observation window is vertical to an observation light axis;
    an illumination window peripheral edge portion which is formed so that a surface having the illumination window is vertical to an illumination light axis which tilts with respect to the observation light axis; and
    a suction port peripheral edge portion which is formed so that a surface having the suction port and the observation window peripheral edge portion forms an angle more acute than a tilt angle of the illumination window peripheral edge portion with respect to the observation window peripheral edge portion, wherein the illumination window peripheral edge portion is provided at a tilt angle of about 8° with respect to the observation window peripheral edge portion, and the suction port peripheral edge portion is provided at a tilt angle of 2 to 3° with respect to the observation window peripheral edge portion.

5. The front cover according to claim 4, wherein a boundary portion between the illumination window peripheral edge portion and the suction port peripheral edge portion is formed into a curved surface shape or a tilt surface shape.

6. The front cover according to claim 4, wherein the observation window peripheral edge portion is formed at an approximately center of a distal end surface of the insertion portion, the illumination window peripheral edge portion is formed so as to tilt backward around the observation window peripheral edge portion, and the suction port peripheral edge portion is formed so as to tilt backward with respect to the illumination window peripheral edge portion.

* * * * *